US00PP20294P2

(12) United States Plant Patent
Chaparro

(10) Patent No.: US PP20,294 P2
(45) Date of Patent: Sep. 15, 2009

(54) PEACH TREE NAMED 'FLORDABEST'

(50) Latin Name: *Prunus persica*
Varietal Denomination: Flordabest

(76) Inventor: Jose X. Chaparro, University of Florida, P.O. Box 110690, Gainesville, FL (US) 32443

( * ) Notice: Subject to any disclaimer, the term of this patent is extended or adjusted under 35 U.S.C. 154(b) by 16 days.

(21) Appl. No.: 12/151,885

(22) Filed: May 9, 2008

(51) Int. Cl.
*A01H 5/00* (2006.01)

(52) U.S. Cl. ..... Plt./197

(58) Field of Classification Search ..... Plt./197
See application file for complete search history.

*Primary Examiner*—Annette H Para

(57) ABSTRACT

A new and distinct variety of nectarine tree, denominated 'Flordabest', has a low winter chilling requirement estimated at 250 chill units (cu). The tree is of medium size, has a moderate vigorous and semi-upright growth habit. It has non-showy, pink flowers, and leaves with reniform glands. Trees of 'Flordabest' are self-fertile and regularly bear heavy annual crops of early season fruit that are large for its ripening season. Fruit are uniformly firm and yellow with melting flesh which are semi-clingstone. Fruit are oval, and uniform with substantially symmetrical shape, and have an attractive 90 to 100% bright red skin. The fruit of 'Flordabest' ripens about 7 to 10 days before 'TropicBeauty' peach in early May at Gainesville, Fla.

1 Drawing Sheet

Botanical classification: *Prunus persica.*—Flordabest.

BACKGROUND OF THE NEW VARIETY

The present invention relates to a new and distinct variety of peach [*Prunus persica* (L.) Batsch] tree adapted to a subtropical (low chill) winter climate. This new tree, named 'Flordabest', produces highly colored, good eating quality, semi-clingstone and melting flesh fruit for fresh market in early May at Gainesville, Fla. Contrast is made to 'TropicBeauty' peach (unpatented), a standard variety, for reliable description. 'Flordabest' is a promising candidate for commercial success in that it has large, attractive red skin, sweet fruit that ripen evenly.

ORIGIN OF THE VARIETY

'Flordabest' peach tree (genotype) originated in a cultivated area of the fruit breeding program located at Gainesville, Fla. where it was tested. The parentage was (Fla. 90-50cn) open-pollinated (unpatented) and of complex origin in the University of Florida breeding program.

'Flordabest' was selected in 2000 because it exhibited yellow, sweet melting flesh, in a large in early season fruit with a bright red skin. It was designated and tested as Fla. 00-04. It was asexually propagated by budding onto 'Flordaguard' (unpatented) seedling rootstock (for root-knot nematode control) at the University of Florida, located in Gainesville, Fla. and determined to have unique tree and fruit characteristics making it worthy for commercial fresh fruit production. There are no known effects of this standard rootstock on this scion cultivar. Asexually propagated plants remained true to the original tree and all characteristics of the tree and the fruit have transmitted for 2 generations.

SUMMARY OF THE VARIETY

The new and distinct variety of peach tree bears fruit that ripen in early May at Gainesville, and has a moderately low chilling dormancy requirement. 'Flordabest' blooms (showy pink flowers) about 5 to 7 days after 'TropicBeauty' peach in early February at Gainesville. The estimated chilling requirement is 250 chill units, based on bloom time. 'Flordabest' tree has fruit that are semi-clingstone and of good flavor and eating quality. The trees are vigorous, productive and without alternate bearing. Trees attain in two years, a height of two meters and a spread of one and a half meters at Gainesville. Terminal growth of up to a half meter annually is common on mature 5-year-old trees with normal pruning to a vase shape. The first fruit ripen in early May at Gainesville or in about 85 days from full bloom, which is about 10 days before 'TropicBeauty'. The fruit are uniformly large, averaging 140 g when properly thinned to a full crop. Ripe fruit have about 90% red skin and there is no red pigment in the flesh at the pit, but there may be some red pigment in the flesh, especially on trees stressed in hot, dry weather. The flower anthers are yellow, and leaf glands are reniform, common characteristics of many standard peach varieties.

DESCRIPTION OF THE DRAWINGS

The accompanying drawing is a color photograph which shows a typical specimen of the fruit, leaf, and stem of the new variety as nearly true as it is reasonably possible to make in a color illustration of this type. The photograph shows an attractive shape and exterior coloration of 6 specimens of fruit above a ruler in side view, stem end view, a blossom end view, a side view showing the suture and a fruit cut longitudinally to show with and without the pit.

DETAILED BOTANICAL DESCRIPTION

The tree, flowers, and fruit may vary in slight detail due to variations in soil type, cultural practices, and climatic condition. The potential for commercial production of fresh fruit by 'Flordabest' is high, due to its attractive red skin over a bright yellow ground color, large fruit of good flavor, and good firmness with even ripening throughout the fruit. The present botanical description is that of the variety grown on 5-year-old trees on 'Flordaguard' rootstock under the ecological conditions prevailing at Gainesville, Fla. Colors (except those in common terms) are described from "The Pantone Book of Color", published by H. N. Abrams, Inc., N.Y. 1990.

Tree:

*Ploidy.*—Diploid.

*Size.*—Trees are medium stature when trained to an open vase form.

*Vigor.*—Moderately vigorous, and must be summer and winter pruned when grown to a vase shape to keep the tree open to get strong fruiting wood in the lower center. Trees respond typically to irrigation and fertilization. Tree growth of 4 to 6 feet in height and 3 to 5 feet in width occurs the first growing season in the field in Florida.

*Density.*—Light to medium in branching habit. Pruning is required to open the tree center to promote sunlight entrance for enhancing fruit color and sugar.

*Form.*—Semi-upright, but easily pruned to vase shape.

*Hardiness*—Hardy with respect to typical north central Florida winters.

*Bearer.*—Very productive annually without alternate bearing observed. Trees are self fertile and must be fruit thinned to avoid limb breakage and obtain large fruit size. Trees annually set several times the number of fruit for a desired crop load.

*Chilling requirement.*—Estimated endodormancy chilling requirement is 250 chill units based on time of bloom and leafing in relation to standard varieties.

Trunk:

*Size.*—Medium trunk diameter attaining 8 cm diameter at a height of 30 cm at the end of 3 years growth at Gainesville.

*Texture.*—Medium smooth, but changes to medium shaggy as tree ages.

*Bark color.*—Older bark gray, Chinchilla (Pantone 17-1109).

*Lenticels.*—High number (24 to 36 per 4 square inches of surface area of trunk) and medium small (4 to 9 mm length perpendicular to the trunk), grey, Sponge (Pantone 16-1118) with the center being yellowish brown, Medal Bronze (Pantone 17-0942).

Branches:

*Size.*—Strong growth of scaffold branches. Fruiting branches are mostly large diameter (4 to 6 mm) and not overly twiggy, resulting in strong fruiting wood. Thus, the tree growth and structure permits easier and faster winter pruning.

*Texture.*—Relatively smooth, numerous lenticels attaining size found on trunk and old scaffolds. Roughness increases with age.

*Color.*—New wood is light green, Endive (Pantone 13-0632); Old wood is more brown, Clay (Pantone 15-1231).

*Crotch angles.*—Angles are selected at 45 to near 90 degrees in first year of tree training. Natural angles are within the normal range of standard varieties for a semi-spreading tree and similar to those of 'Tropic-Beauty'.

Leaves:

*Size.*—Medium; 17 to 19 cm length, including the petiole; 3.5 to 4.1 cm width. Measurements were made on vigorous upright shoots of summer growth.

*Thickness.*—Regular and average for commercial nectarine varieties. Not noticeably unusual.

*Form.*—Lanceolate.

*Apex.*—Acute.

*Margin.*—Serrulate, slightly undulate.

*Base.*—Cuneate.

*Surface.*—Upper, glabrous; Lower, medium large veins that are pinnately netted.

*Color.*—Lower surface is green, Peridot (Pantone 17-0336); Upper surface is slightly darker green, Vineyard Green (Pantone 18-0117).

*Glands.*—Usually 2, small reniform glands mostly on lower leaf blade, but occasionally on petiole. Leaf glands on young leaves are yellowish green, Sulphur (Pantone 14-0755), darkening to Avocado (Pantone 18-0430) on older leaves in mid-summer. Size averages between 1 mm in length and 0.6 mm in length.

*Petiole.*—About 1 cm (0.8 to 0.9 cm) length; 1.6 mm diameter. Light green, Beechnut (Pantone 14-0425) on older leaves of summer. Grooved longitudinally.

*Stipules.*—Medium (equal to most commercial peach varieties), usually 2 per bud, and abscising just before leaf becomes full size in summer growth. Color at full size is green, Leek Green (Pantone 15-0628).

*Arrangement.*—Alternate.

Flower buds:

*Hardiness.*—Hardy with respect to north central Florida winters (16F minimum observed).

*Abundance.*—Very high due to shorter than average internode length. Most buds set fruit in absence of spring frosts and show little evidence of bud drop.

*Size.*—Medium, average 3.5 mm length in mid winter.

*Form,*—Plump, conic and free.

*Surface.*—Pubescent scales.

*Color.*—Brown, Stucco (Pantone 16-1412) in late summer.

Flowers:

*Blossom period.*—Blooms 5 to 7 days after 'Tropic-Beauty' peach— average 50% bloom February 8 to 12 most years at Gainesville, but occurring over a 7–10 day period. Time and length of bloom are dependant on ambient temperature.

*Aroma.*—None observed.

*Flower density.*—Abundant, varying 1 to 3 per node, but usually 2.

*Type.*—Showy, but location and seasonally variable within the range of commercial showy varieties. Average flower diameter is 4 cm. Average petal length, 20 mm; Width, 12 mm. Texture smooth. Margins are undulate and wavy.

*Color.*—Pink, Almond Blossom (Pantone 13-2006) at flower opening.

*Flower parts.*—Stamens and pistil size, shape and color are within the range of standard commercial varieties. There are 5 sepals and petals. Sepals average 5 mm length and 4 mm wide at attachment to calyx cup and rounded at the distal end. Sepals are green, Piquant Green (Pantone 17-0235) on the interior and green, Cameo Green (Pantone 14-6312) on the exterior with a smooth pubescent margin. Sepals are pubescent and petals are glabrous. Pistils are usually 1 per flower and straight (without curls or curves) just prior to flower opening. Pistil length (from tip of stigma to base of ovary) averages 15 mm. Pistils are light green, Pale Star (Pantone 12-0626). Flower pedicel is 1 to 2 mm length.

*Calyx cup.*—Medium small in the size range of commercial varieties. Calyx cup diameter is 5 mm at the time of flower opening. Calyx exterior is red, Cardinal (Pantone 18-1643) and interior is orange, Persimmon Orange (Pantone 16-1356).

*Stamen.*—Anthers are yellow, Amber Yellow (Pantone 13-0942) at flower opening. Number of anthers varies from 27 to 36. Filaments are light green, Pale Star (Pantone 12-0626) and length is 7 to 9 mm.

*Pollen.*—Abundant and bright yellow, Snapdragon (Pantone 13-0840), common to many peach varieties.

*Fertility.*—Fully self fertile, and no cross pollination is required. Fruit set is abundant.

Fruit:

*Maturity when described.*—Tree ripe, May 5, 2006 at Gainesville.

*Date of picking.*—First, Apr. 26, 2006; Last,–May 12, 2006 at Gainesville.

*Size.*—Uniform, medium large (large size for early mid-season maturity at 120 to 150 g). Varies with fruit number per tree, soil type, climatic conditions and cultural practices. Average equatorial diameter.— 2⅜ inches (60 mm). Average polar length (stem to distal end).— 2⅝ inches (65 mm).

*Pedicel size and color.*—Length is approximately 7 mm; Width is approximately 3 mm. Color is green, Mellow Green (Pantone 12-0426).

*Longitudinal section form.*—Strongly oval.

*Transverse section through diameter.*—Round.

*Suture.*—Shallow and inconspicuous except for a crease on the stem end of the fruit.

*Ventral surface.*—Usually rounded.

*Base.*—Slightly cordate.

*Apex.*—Usually rounded to slightly obtuse.

*Crater at stem attachment.*—Flaring circular with slight suture crease at the stem end. Depth is 6 to 9 mm; breadth is 18 mm at top and 4 mm at pedicel attachment.

Skin:

*Thickness.*—Medium in comparison to commercial peach varieties.

*Texture.*—Medium in comparison to commercial peach varieties.

*Tenacity.*—Tenacious to flesh.

*Color.*—Dark red, Damson (Pantone 18-1716), over nearly 100% of skin. Ground color is yellow, Beeswax (Pantone 14-0941). Fruit exposed to sunlight have a higher degree of enhanced red skin.

*Tendency to crack.*—None observed.

*Taste.*—No astringency observed.

*Epidermis.*—Pubescent, but slightly shorter than 'TropicBeauty'.

Flesh:

*Ripens.*—Evenly within each fruit.

*Texture.*—Firm, juicy, melting when fully ripe.

*Fibers.*—Very fine, small, tender, and abundant.

*Aroma.*—Moderate and in the middle range of commercial peach varieties.

*Eating quality.*—Good, moderately sweet, slightly acid. Soluble solids vary from 11.2 to 14 brix at 3 and 2.4 kg penetrometer (3/16 inch tip) firmness, respectively.

*Juice.*—Abundant.

*Color.*—Yellow, Golden Queen (Pantone 13-0939), with red flecks, Teaberry (Pantone 18-1756) in the flesh, especially on stressed trees under dry, hot conditions. There is no red at the pit.

*Browning by oxidation.*—Not detectable on tree ripe fruit beginning to soften.

*Amygdalin.*—Undetected.

Stone:

*Type.*—Semi-clingstone.

*Size.*—Medium small: average length is 25 mm; average width is 21 mm; average thickness is 16 mm; average wall thickness is 5–6 mm.

*Color.*—Light Brown, Topaz (Pantone 16-1150) when flesh is freshly cut.

*Form.*—Oblong. Base. — Straight. Apex. — Acute. Sides. — Near equal. Surface. — Irregularly furrowed toward the ventral edge, pitted from base to apex. Ridges. — Jagged toward the base. Tendency to split. — None observed.

*Seed.*—Bitter (amygdalin is abundant) kernel. Viable if stratified upon removal from fruit at harvest, and without drying. Kernel is brown, Sunflower (Pantone 16-1054) when first removed from ripe fruit. Size is 15 mm length, 8 mm wide and 5 mm thick. Shape is acute tip with obtuse base and overall ovate shape.

Use— Fresh; dessert.

Resistance to disease— High resistance to bacterial spot incited by *Xanthomonas campestris* pv. *pruni* (Pers.) Diet Resistance to other fruit and tree diseases are within the range for commercial peach cultivars in Florida. No unusual resistance or susceptibility to insects and diseases noted.

Keeping quality.— Excellent after 8 days at 2C and with minimal bruises or scarring appear on skin.

Shipping quality.— Degree of firmness at harvest and firmness retained in refrigeration for 8 days at 2C, with no internal breakdown of flesh or appreciable loss of eating quality, indicates fruit should be highly acceptable for shipping.

We claim:

1. A new and distinct peach tree as illustrated and described, characterized by a low chilling requirement, and bearing fruit having firm, yellow, sweet, and melting, semi-clingstone flesh of high eating quality and an attractive, high percentage red skin with fruit ripening in early May or about 7 to 10 days before 'TropicBeauty' at Gainesville, Fla.

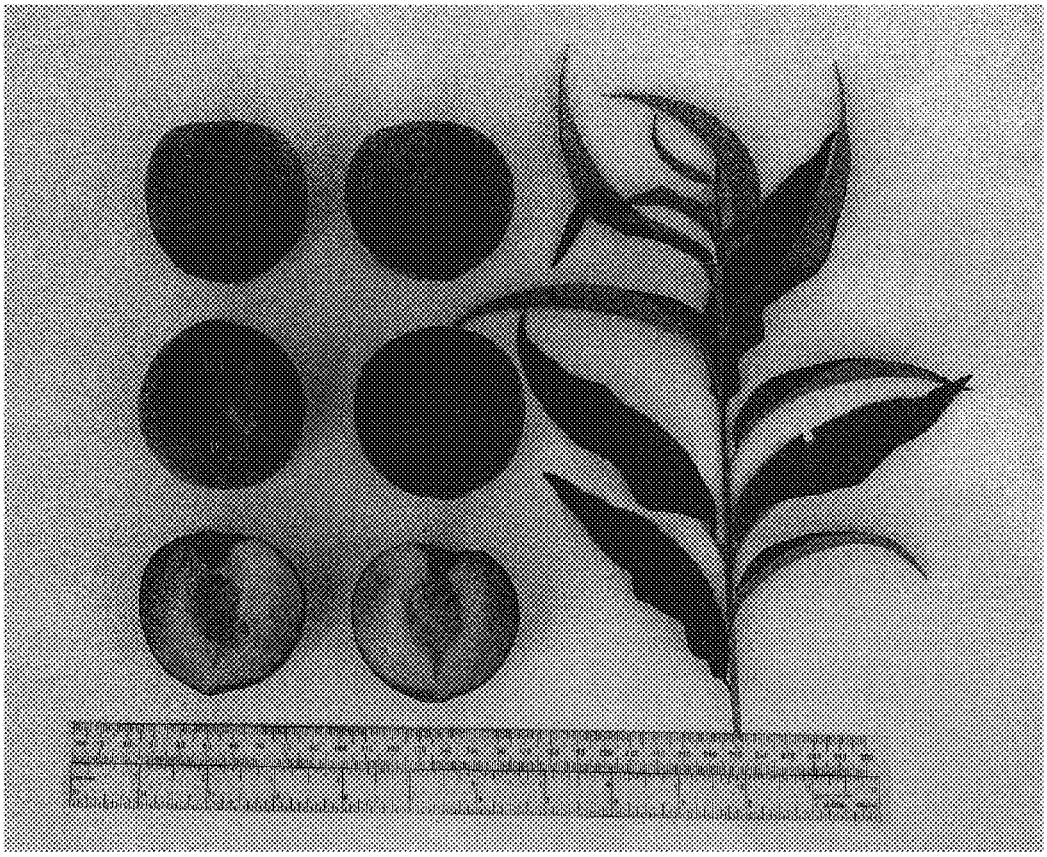

* * * * *